United States Patent
Hernandez Castanedas et al.

(10) Patent No.: US 10,045,690 B2
(45) Date of Patent: Aug. 14, 2018

(54) METHOD FOR DETERMINING WAVE-FRONT ABERRATION DATA OF A TO-BE-TESTED OPTICAL SYSTEM

(71) Applicant: Essilor International, Charenton-le-Pont (FR)

(72) Inventors: Martha Hernandez Castanedas, Charenton-le-Pont (FR); Gildas Marin, Charenton-le-Pont (FR); Larry Thibos, Charenton-le-Pont (FR); Tao Liu, Charenton-le-Pont (FR)

(73) Assignee: Essilor International, Charenton-le-Pont (FR)

( * ) Notice: Subject to any disclaimer, the term of this patent is extended or adjusted under 35 U.S.C. 154(b) by 214 days.

(21) Appl. No.: 14/897,205

(22) PCT Filed: Jun. 9, 2014

(86) PCT No.: PCT/EP2014/061933
§ 371 (c)(1),
(2) Date: Dec. 9, 2015

(87) PCT Pub. No.: WO2014/198678
PCT Pub. Date: Dec. 18, 2014

(65) Prior Publication Data
US 2016/0135678 A1 May 19, 2016

(30) Foreign Application Priority Data
Jun. 10, 2013 (EP) ..................................... 13305781

(51) Int. Cl.
*A61B 3/10* (2006.01)
*A61B 3/00* (2006.01)

(52) U.S. Cl.
CPC .......... *A61B 3/1015* (2013.01); *A61B 3/0025* (2013.01)

(58) Field of Classification Search
CPC ..... A61B 3/1015; A61B 3/0025; A61B 3/103; G01M 11/00242; G01M 11/0264; G01M 11/025; G01M 11/0257; G01J 2009/002
See application file for complete search history.

(56) References Cited

U.S. PATENT DOCUMENTS

| 2006/0126019 A1* | 6/2006 | Liang ................... A61B 3/1015 |
| | | 351/246 |
| 2009/0009717 A1 | 1/2009 | Barrett et al. |
| 2013/0092816 A1* | 4/2013 | Barrett ..................... G01J 9/00 |
| | | 250/201.9 |

FOREIGN PATENT DOCUMENTS

WO    WO 2010/005458    1/2010

OTHER PUBLICATIONS

J. Liang et al., "Objective Measurement of Wave Abberations of the Human Eye with the Use of a Hartmann-Shack Wave-Front Sensor", Journal of the Optical Society of America A, vol. 11, No. 7, pp. 1949-1957, Jul. 1, 1994.

* cited by examiner

*Primary Examiner* — William R Alexander
*Assistant Examiner* — Ephrem Mebrahtu
(74) *Attorney, Agent, or Firm* — Oblon, McClelland, Maier & Neustadt, L.L.P.

(57) ABSTRACT

A method for determining wave-front aberration data of a to-be-tested optical system comprising the steps of: a) providing a wave-front sensing image of light received from the tested optical system; b) providing a model representative of the optical system with at least an optical parameter representative of said model; and c) optimizing a set of wave-front coefficient data and said at least optical parameter of said model according to a merit function calculating the merit function comprises the steps of generating a wave-front sensing modeled image of light received from said model by the at least optical parameter and the set of wave-front coefficient data, and calculating a criteria based on shape parameter data of the wave-front sensing image and shape parameter data of the wave-front sensing modeled image, so as to obtain wave-front aberration data of the tested optical system.

15 Claims, 3 Drawing Sheets

Fig. 3B
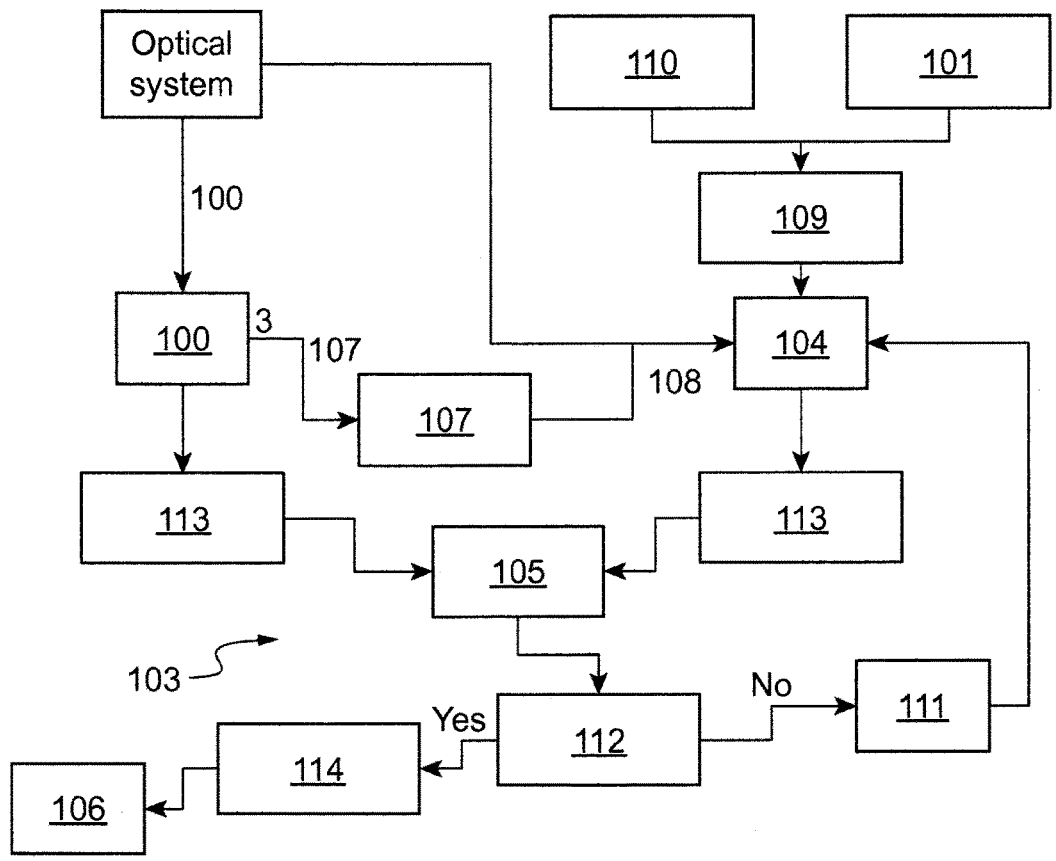
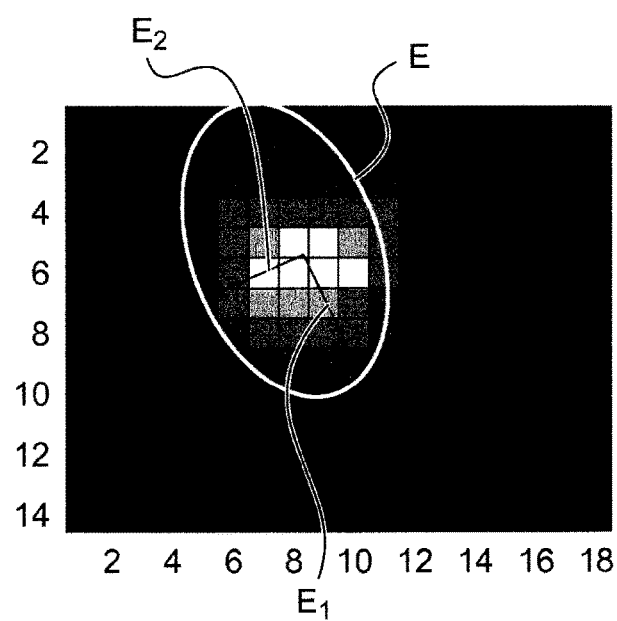
Fig. 4

Fig.5
| C20(micron) | | Anterior | Posterior |
|---|---|---|---|
| Condition | Observed image (G)* | 0 (0D) | 0.9093(-0.7D) |
| | Start value(centroid) | 0.4547 ||
| Results | Model image (H)** | 0.001 | 0.9099 |
| | SSE | 0.0074 ||
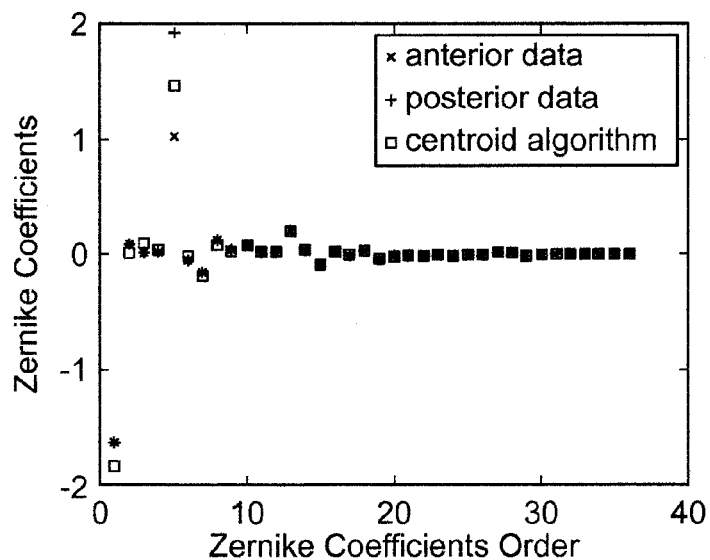
Fig.6
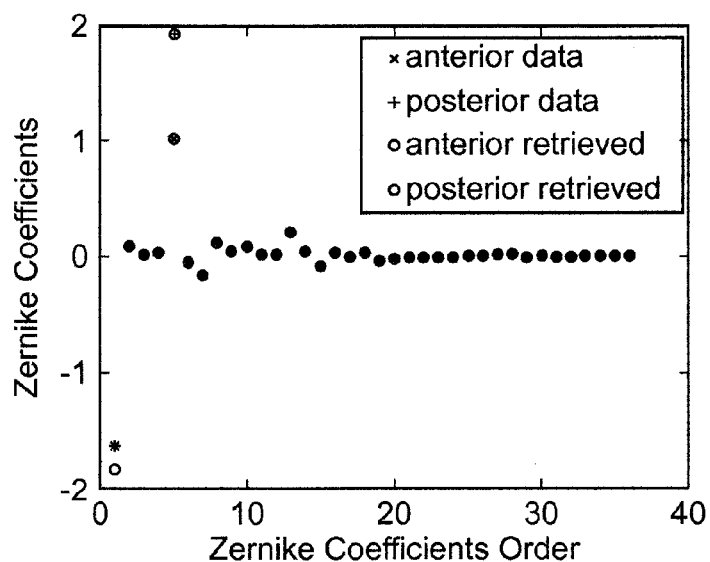
Fig.7

METHOD FOR DETERMINING WAVE-FRONT ABERRATION DATA OF A TO-BE-TESTED OPTICAL SYSTEM

RELATED APPLICATIONS

This is a U.S. national stage application under 35 USC § 371 of International application No. PCT/EP2014/061933 filed on Jun. 9, 2014. This application claims the priority of European application no. 13305781.0 filed Jun. 10, 2013, the entire content of which is hereby incorporated by reference.

FIELD OF THE INVENTION

The present invention relates to a system and a method for determining wave-front aberration data of a to-be-tested optical system from image data.

BACKGROUND OF THE INVENTION

In the field of ophthalmic aberrometry, wavefront aberration data provides a comprehensive description of human eye's optical properties, from which the refractive error as well as image quality metrics can be calculated.

Wavefront technology is based primarily on precise measurements of eye's wave aberration data using a device called wavefront sensor.

Numerous commercial wavefront sensors for the eye are available with most based on Shack-Hartmann wavefront sensor technology, as described in Liang et al. 94', "Objective measurement of wave aberrations of the human eye with the use of a Hartmann-Shack wave-front sensor," J. Opt. Soc. Am. A, vol. 11, no. 7, p. 1949, July 1994.

FIG. 1 illustrates some principal elements of a basic configuration of the Shack-Hartmann wavefront sensor 10.

A measurement instrument employing the Shack-Hartmann wavefront sensor injects incoming wavefront light into a human eye which focuses on the retina of the eye and scatters back toward the measurement instrument.

The Shack-Hartmann wavefront sensor consist of an array of lenslets 11 in the plane conjugated to the pupil of the human eye and an optical detector 12 such as a charge-coupled device (CCD).

This incoming wavefront light is imaged onto the lenslets array 11 and produces a wavefront sensor image 13, 14 as an array of focus spots 13a, 14a formed on the focal plane of the optical detector 12 and recorded by the optical detector 12.

The locations of the focus light spots 13a, 14a are sensed and used to derive wavefront slope at each lenslet 11.

As the wave-front slope at each lenslet changes, each focus light spot 14a deviates relative to its reference location in the reference pattern 13 (i.e., the locations that result when a true plane wave is applied to the lenslet array) proportionally.

Wave-front aberrations data and wavefront reconstruction may be derived by calculating the centroid of each focus light spot 14a, and fitting the local slopes to a set of basis function such as Zernike polynomials.

The image quality is essential to ensure the accuracy of the optical measurements and the quality of the wavefront reconstruction.

Indeed, inaccurate focal light spot distributions, inaccurate focus light spot location data and/or inaccurate focus light spot intensity data will introduce errors into the estimate of the wave aberration data to the extent that it displaces the centroid computed for each focus light spot.

Wavefront reconstructed from the centroids of the inaccurate focus light spots provides an improper description of the optical aberrations of the tested optical system.

Wavefront reconstruction from conventional algorithms can be compromised and degraded by several artifacts that affect the wavefront sensing image data quality by incorporating spurious aberrations.

Conventional algorithms have proposed solutions to manage some artifacts such as the specular reflex from cornea.

However, others artifacts are underestimated.

For example, this is the case for the following artifact.

Conventional wavefront reconstruction algorithms assume that the wavefront sensing image is produced by light reflected from a single layer of fundus, which contradicts OCT (optical coherence tomography) results showing multiple layers contribute to the reflection.

More precisely, conventional wavefront reconstruction algorithms assume that the wavefront sensing image is produced by light reflected from a single point source which is located at a constant distance from the light-receiving layer in the tested eye.

In fact, the exact position of the point source is not mastered. Indeed, the retina is a rather thick reflector and multilayer and a probe beam is simultaneously reflected by multiple layers of the retina.

The focus light spots resulting from different reflective layers are laterally displaced and axially superimposed, which gives rise to spot elongation in the wavefront sensing image.

Therefore, conventional wavefront reconstruction algorithms lead to errors of unknown magnitude and wavefronts reconstructed will introduce spurious amounts of aberrations such as spherical aberration and defocus.

Thus, the management of noise and artifacts in the wavefront sensor data that would contaminate the measurements is a key issue.

There is a need to a method for determining wave-front aberration data to overcome the degrading effects of aberrations in image data and to respond to measurement accuracy and precision requirements.

SUMMARY OF THE INVENTION

One object of the invention is to provide a method for determining wave-front aberration data of a to-be-tested optical system that responds to failures of conventional methods.

Another object of the invention is to provide a method for determining wave-front aberration data of a to-be-tested optical system that allow to reduce the impact of artifacts degrading the quality of spot patterns and hence improve the wavefront aberrations measurements.

Another object of the invention is to provide a method for determining wave-front aberration data of a to-be-tested optical system providing accurate measurements of eye's wave aberration for reliable vision correction and vision diagnosis.

To this end, one aspect of the invention is directed to a method for determining wave-front aberration data of a to-be-tested optical system comprising the steps of:
a) providing a wave-front sensing image of light received from the tested optical system;
b) providing a model representative of the optical system with at least an optical parameter representative of said model c) optimizing a set of wave-front coefficient data and said at least optical parameter of said model according to a merit function wherein the calculation of said merit function comprises the steps of:

generating a wave-front sensing modeled image of light received from said model by means of said at least optical parameter and said set of wave-front coefficient data;

calculating a criteria based on shape parameter data of the wave-front sensing image and shape parameter data of the wave-front sensing modeled image, so as to obtain wave-front aberration data of the tested optical system.

Advantageously, the method according to an embodiment of the invention offers a global algorithm using a model eye and shape parameters data which overcome the degrading effects of aberrations in wavefront sensing image data and respond to aberrations measurement accuracy requirements.

According to further embodiments which can be considered alone or in combination:

said wave-front sensing image comprises an array of sensed focus light spots and;

said wave-front sensing modeled image comprises an array of modeled focus light spots and;

the calculation of the criteria comprises the step of calculating a difference at least between a shape parameter of the sensed focus light spots and of the modeled focus light spots.

said model is an eye model comprising n reflective layers, n>1.

at least two of the reflective layers reflect light with different directionalities.

generating the wave front sensing modeled image comprises:

obtaining a wave-front sensing image of light received from each illuminated reflective layer of said eye model and;

generating a wave-front sensing composite modeled image from the wave-front sensing images of the n reflective layers.

the optical parameter characterizing said eye model is representative of the relative position between two reflective layers.

the step of obtaining wave-front aberration data comprises:

selecting a reflective layer of said eye model and obtaining wave-front aberration data from the set of wave-front coefficient data being characteristic of said selected reflective layer.

the step c) further comprises:

a shape parameter data determining step during which a plurality of spot descriptors are generated, each spot descriptor characterizing shape parameter data of a respective focus light spot and, each spot descriptor including an α order moment shape descriptor, α>1, a Fourier shape descriptor or a vector field descriptor.

the shape parameter data determining step comprises:

measuring pixel intensity values for each focus light spot, generating second moment data of the pixel intensity values for each focus light spot as a spot descriptor of the respective spot.

The merit function is defined with the following expression (9):

$$F = \sqrt{\sum_{k=1}^{L} \sum_{i=1}^{4} (sm_{ik} - ss_{ik})^2} \quad (9)$$

where:

L is the number of focus light spots in the wave-front sensing image;

sm is a second moment of pixel intensity values for a sensed focus light spot;

ss is a second moment of pixel intensity values for a modeled focus light spot.

the method, further comprises:

a repositioning step of a pupil of said model so as to match the position of a pupil of the tested optical system as it is observed in the provided wave-front sensing image.

the repositioning step comprises:

a repositioning step of the array of modeled focus light spots of said model so as to match the position of the array of sensed focus light spots of the tested optical system as it is observed in the provided wave-front sensing image.

According to a further aspect, the invention relates to a method to measure the aberrations of an human eye comprising:

illuminating the human eye under test with light produced by a light source, performing the method for determining wave-front aberration data of the tested human eye mentioned above, determining the aberration's corrections for the tested human eye from the determined wave-front aberration data.

According to a further aspect, the invention relates to a method to correct the aberrations of an human eye comprising:

illuminating the human eye under test with light produced by a light source, performing the method for determining wave-front aberration data of the tested human eye mentioned above, determining the aberration's corrections for the tested human eye from the determined wave-front aberration data, receiving said aberration's corrections:

to control a compensating optical device to provide compensation for said determined wave-front aberration data of the tested human eye or;

to manufacture lenses that correct said aberrations or;

to perform surgery on the tested human eye to correct said aberrations.

According to a further aspect, the invention relates to a computer program product comprising one or more stored sequences of instructions that are accessible to a processor and which, when executed by the processor, causes the processor to carry out the acquisition, parameter determining and adaptive steps of the method according to the invention.

Another aspect of the invention relates to a computer readable medium carrying one or more sequences of instructions of the computer program product according to an embodiment of the invention.

Another aspect of the invention relates to a program which makes a computer execute the method according to an embodiment of the invention.

Another aspect of invention relates to a computer-readable storage medium having a program recorded thereon; where the program makes the computer execute the method according to an embodiment of the invention.

Another aspect of the invention further relates to a device comprising a processor adapted to store one or more sequence of instructions and to carry out at least one of the steps of the method according to an embodiment of the invention.

Unless specifically stated otherwise, as apparent from the following discussions, it is appreciated that throughout the specification discussions utilizing terms such as "computing", "calculating", "generating", or the like, refer to the action and/or processes of a computer or computing system, or similar electronic computing device, that manipulate and/or transform data represented as physical, such as electronic, quantities within the computing system's registers and/or memories into other data similarly represented as physical quantities within the computing system's memories, registers or other such information storage, transmission or display devices.

Embodiments of the present invention may include apparatuses for performing the operations herein. This apparatus may be specially constructed for the desired purposes, or it may comprise a general purpose computer or a Field Programmable Gate Array ("FPGA") or Digital Signal Processor ("DSP") selectively activated or reconfigured by a computer program stored in the computer. Such a computer program may be stored in a computer readable storage medium, such as, but is not limited to, any type of disk including floppy disks, optical disks, CD-ROMs, magnetic-optical disks, read-only memories (ROMs), random access memories (RAMS) electrically programmable read-only memories (EPROMs), electrically erasable and programmable read only memories (EEPROMs), magnetic or optical cards, or any other type of media suitable for storing electronic instructions, and capable of being coupled to a computer system bus.

The processes and displays presented herein are not inherently related to any particular computer or other apparatus. Various general purpose systems may be used with programs in accordance with the teachings herein, or it may prove convenient to construct a more specialized apparatus to perform the desired method. The desired structure for a variety of these systems will appear from the description below. In addition, embodiments of the present invention are not described with reference to any particular programming language. It will be appreciated that a variety of programming languages may be used to implement the teachings of the inventions as described herein.

BRIEF DESCRIPTION OF THE DRAWINGS

Other features and advantages of the present invention will become apparent from the following description of non-limitative embodiments, with reference to the attached drawings in which:

FIGS. 3A and 3B represent a flowchart illustrating an embodiment of a method according to the invention;

FIG. 4 illustrate a second moment descriptor superimposed on a light focus spot;

FIGS. 5 to 7 show, respectively, a table and diagrams illustrating wavefront coefficients data derived from a conventional centroid algorithm and from the method according to the invention.

DETAILED DESCRIPTION OF THE DRAWINGS

Method of the invention as described below can be employed in a variety of different measurement instruments. Exemplary embodiments will be described in some detail below so as to illustrate various aspects and advantages of these methods. However, it should be understood that the principles involved in these methods can be employed in a variety of other measurement instruments which employ image data.

Figure 1:
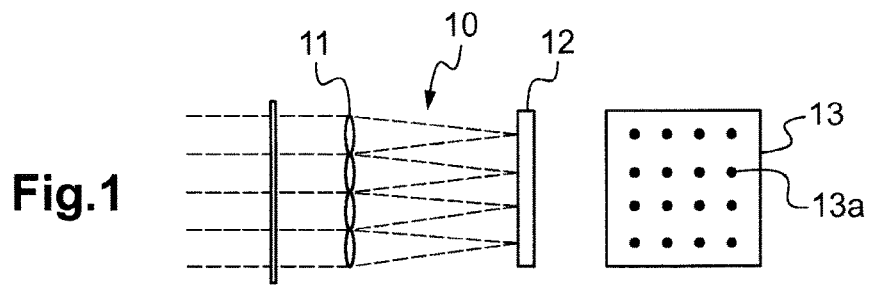
FIG. 1 represents a schematic diagram of a Hartmann-Shack sensor and the related wavefront sensing image for an ideal eye without aberrations and for a human eye with aberrations.
Figure 2:
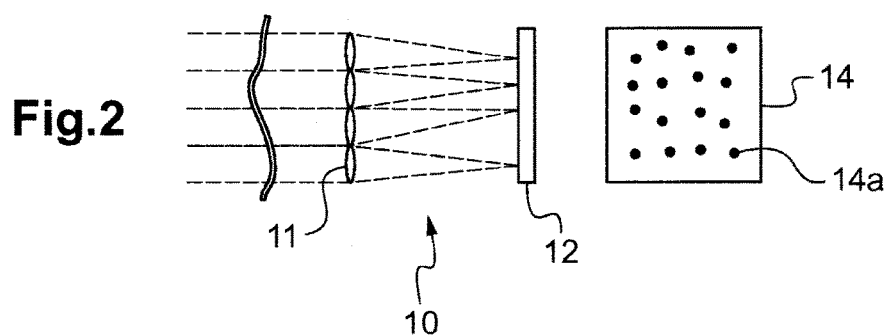
FIG. 2 represents a schematic diagram of a measuring instrument with a wavefront sensor, configured for measuring wave aberration of a multilayer retina of a human eye.

FIG. 2 illustrates one embodiment of a measurement instrument 20 employing a wavefront sensor 21.

Among other components, the measurement instrument 20 includes a probe beam, an optical relay system 22, a beam splitter 25, a processor 23 and a storage unit 24 associated with the processor 23.

The light source generates a compact light beam at the retina of the eye to be tested. The compact light beam illuminates the eye's retina and is diffusely reflected by the retina.

A distorted wavefront is relayed by the optical relay system 22 to a Hartmann-Shack wavefront sensor 21.

The optical relay system 22 consists of lenses L1 and L2.

The Hartmann-Shack wavefront sensor 21 comprises a lenslet array 21a and an image sensor 21b.

The lenslet array 21a converts the distorted wavefront to an array of focus spots as a wavefront sensing image on the image sensor 21b.

The wavefront sensing image data are supplied to the processor 23 and associated storage unit 24 to be stored or processed by a image processing unit 26 to determine measurement of wavefront aberrations data of the light beam received from the retina.

The processor 23 may be configured to run algorithms for performing the processing steps of the method according to the invention.

The processor 23 may also include a model unit 27 which generate an optical system model and the related image data, as described below with reference to FIG. 2.

One of skill in the art will recognize that, once the wavefront sensing image data are received by the processor 23, the processing steps may be performed by the method according to the invention described below.

In an exemplary embodiment, the human eye is the optical system to be tested. It should be understood that the principles involved in these methods can be employed in a variety of other optical systems.

Figure 3A:
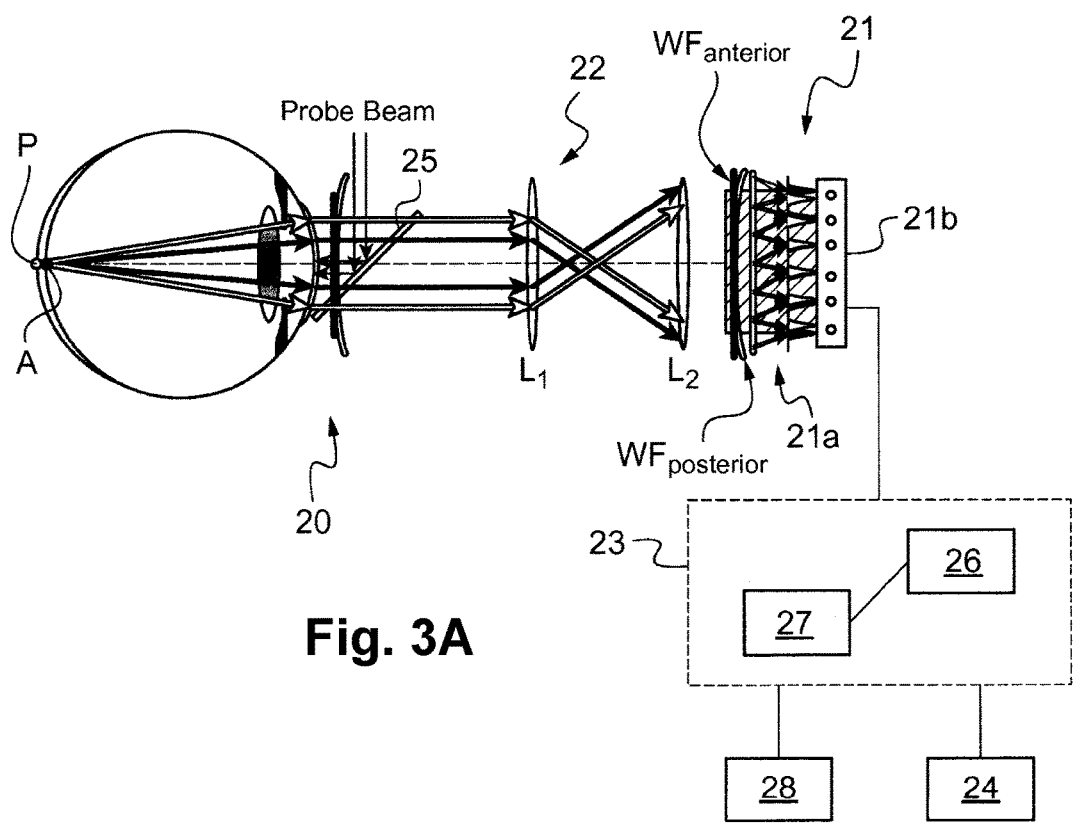

According to an embodiment of the invention illustrated in FIG. 3, the method for determining wave-front aberration data of a to-be-tested human eye comprises:

a wave-front sensing image providing step 100 during which a wave-front sensing image of light received from the tested human eye is provided;

a model providing step 101 during which a model representative of the human eye with at least an optical parameter representative of said model are provided;

an optimizing step 103 during which a set of wave-front coefficient data and said at least optical parameter of said model are optimized according to a merit function wherein the calculation of said merit function comprises the steps of:

generating a wave-front sensing modeled image 104 of light received from said model by means of said at least optical parameter and said set of wave-front coefficient data;

calculating a criteria (step 105) based on shape parameter data of the wave-front sensing image and shape parameter data of the wave-front sensing modeled image and a wavefront aberration data determining step 106 during which wave-front aberration data of the tested human eye are obtained.

In an embodiment, during the wave-front sensing image providing step 100, a wave-front sensing image comprises an array of sensed focus light spots is obtained.

The wave-front sensing image providing step 100 may be implemented with the measurement instrument illustrated in FIG. 2 discussed above and, in particular, with an Hartmann-Shack sensor.

As illustrated in FIG. 3, in a next step 107, a first set of wave-front coefficient data from the wave-front sensing image are derived using a first calculation algorithm.

In an embodiment, the first set of wave-front coefficient data deriving step comprises the calculation of a location of the sensed focus light spots in the wavefront sensing image using a centroid calculation algorithm, known from the State of Art.

Such algorithm comprises a first step which is a centroiding step of the sensed focus light spots.

During said step, the centroid of the entire wavefront sensing image pattern is found and the localization of a focus light spot close to it is implemented. Then, the whole image area is divided into many small regions within which only one sensed focus spot exists. The location of the light focus spot in each lenslet is determined by the centroid of a light distribution.

The local slopes or partial derivatives of the tested wave-front are then detected by determining light focus spot displacement relative to a calibrated reference.

In a next step, wavefront reconstruction is initiated.

In an embodiment, modal wave front estimation with Zernike polynomials may be implemented to reconstruct the wavefront.

By processing the tested partial derivatives, the Zernike modes are fitted and estimated Zernike coefficients can be obtained as first set of wave-front coefficient data.

As illustrated in FIG. 2, during the model representative of the human eye providing step 101, an eye model comprising n reflective layers, n>1 is defined.

The eye model may be a discrete or continuous multilayer model.

In a preferred embodiment, the eye model is a dual-layer discrete retina model as illustrated in FIG. 2. FIG. 2 shows the two layers, namely an anterior layer A and a posterior layer P.

Furthermore, in a non limitative example, the optical parameter characterizing the eye model is representative of the relative position between the two reflective layers.

According to a further aspect of the invention, at least two of the reflective layers may reflect light with different directionalities.

Advantageously, according to the present invention, the eye model takes the multiple layer reflection into account. As illustrated in FIG. 2, wavefront (WF anterior) from anterior layer A and wavefront (WF posterior) from posterior layer P are taken into account. To the contrary, conventional wavefront reconstruction algorithm assumes the focus spot data image was produced by light reflected from single layer of fundus of a human eye.

Furthermore, advantageously, spurious amounts of spherical aberration and defocus that may be introduced by conventional centroid algorithms are reduced.

Regarding the wave-front sensing modeled images of the eye model, they may be simulated with the same configuration as the measurement instrument of FIG. 2 used for the wave-front sensing tested images.

In a non limitative example, the model may be implemented assuming a unit magnification relay telescope, an array of 10×10 microlenses of width 0.4 mm with 24 mm focal length, a pupil size scaled to 4 mm at wavefront sensor plane. 6 mm diameter pupil may be chosen to mimic the dilated eye.

The model may also include higher-order aberrations typical of human eyes.

In addition, the wave-front sensing modeled image may comprise an array of modeled focus light spots.

Furthermore, as illustrated in FIGS. 2 and/or 3, the model unit 26 which generate the wavefront sensing modeled images receives as input parameters (steps 108/109):
  a initial set of wave-front coefficient data (step 108),
  a list of wave-front coefficient data to vary selected in step 110 and
  an initial value of the optical parameter characterizing the multilayer eye model (step 109).

According to a particularly advantageous embodiment of the invention, the initial set of wave-front coefficient data is the first set of wave-front coefficient data generated in step 107 using a first calculation algorithm. This first set of data provides a reasonable estimate for initial parameters.

The step 104 of generation of a wave-front sensing modeled image of light received from said multilayer eye model 101 comprises the following substeps:
  generating a wave-front sensing image of light received from each illuminated reflective layer of said eye model 101 and;
  generating a wave-front sensing composite modeled image from the wave-front sensing images of the n reflective layers.

More precisely, in the embodiment of a bi-layer eye retina model illustrated in FIG. 2, the step of generating wavefront sensing composite modeled image takes into consideration a wavefront reflected from the more anterior layer A denoted as Wa(x,y) and a wavefront reflected from the more posterior layer P denoted as Wp(x,y).

A substep of calculating the individual light focus spot intensity, which is the point spread function of the sub-wavefront, using the wavefront over a subaperture representing a microlens as shown in equations (1) and (2) is implemented.

$$I_a(i,j)=|FFT(W_a(x,y)|x,y,\text{subaperture of microlens}(i,j))|^2 \quad (1)$$

$$I_p(i,j)=|FFT(W_p(x,y)|x,y,\text{subaperture of microlens}(i,j))|^2 \quad (2)$$

Where $I_a(i,j)$ and $I_p(i,j)$ are the light focus spots intensity at ith row and jth column of focus spots array for anterior and posterior respectively. x and y are the coordinates in the plane of the lenslet array.

More particularly, to generate the wave-front sensing composite modeled image, the intensity of the composite spot I(i,j) may be considered as the sum of intensity of each reflective layer, as shown in equation (3)

$$I(i,j)=j)=I_a(i,j)+I_p(i,j) \quad (3)$$

Advantageously, the computation is simplified.

In an alternative embodiment, the intensity of the composite spot I(i,j) may be considered as the sum of intensity produced by each reflective layer with proper weights.

In an example, the weight may be proportional to the reflectivity of the related layer and could be obtained from OCT measurement.

In another embodiment, the weight may also be representative of the directionalities in the reflectivity of each layer.

In a next step, the wave-front sensing composite modeled image Img(x,y) is generated by mapping the composite spots to the corresponding position, as shown in equation (4)

$$Img(x, y) = \sum_{i,j=1}^{M,N} I(i, j)d(i-x, j-y) \quad (4)$$

Where $$d(i-x, j-y) = \begin{cases} 1 & x = i, y = j \\ 0 & \text{otherwise} \end{cases}$$

In addition, the method further comprises a repositioning step (non illustrated) during which a pupil of the multilayer eye model 101 is repositioned so as to match the position of a pupil of the tested human eye as it is observed in the provided wave-front sensing image.

More precisely, the processor 23 initiate a repositioning step of the array of modeled focus light spots so as to match the position of the array of sensed focus light spots of the tested human eye.

As illustrated in FIG. 3, the optimizing step 103 comprises the calculation (step 105) of a merit function wherein the merit function comprises a difference between wavefront sensing tested images and wavefront sensing modeled images.

The merit function C may be given by the following equation (5)

$$C = \sum_i \frac{(g_i - h_i)^2}{h_i} \quad (5)$$

Where $g_i$, $h_i$ are the wavefront sensing tested images and wavefront sensing modeled images intensities in pixel i.

The calculation 105 of the merit function is performed by iteratively adjusting (step 111) the optical parameter characterizing the eye model and a set of wave-front coefficient data until a predefined condition 112 is satisfied.

The predefined condition may include one or more of: minimization of the merit function; maximization of the merit function; reaching a preset number of iterations; reaching a value of the merit function equal to or beyond a preset threshold value; and, reaching a value of the merit function within an acceptable error limit.

In a preferred embodiment, the merit function is minimized by optimising the set of wavefront coefficient data and the optical parameter of the eye model.

In one embodiment, the set of wavefront coefficient data may be Zernike coefficients that represent the wavefront and the optical parameter may be the axial separation between two reflective layers of the eye model 101.

It should be noted that the set of wavefront coefficient data may comprise only one coefficient or several coefficients chosen as a variable during optimization.

Furthermore, similar to chromatic aberration (different wavelengths produce different Zernike Coefficient for defocus mode while almost constant for other terms), the difference in defocus terms for the two reflective layers should be significantly greater that the corresponding difference for other modes.

Accordingly, in a non limitative embodiment, defocus was firstly optimized, then the other terms in the natural sequence of Zernike orders.

According to a further aspect of the invention, the method of the invention may recover low order and/or high order aberration coefficients.

In a preferred embodiment, the wavefront coefficients data should be optimized sequentially from low order to high order instead of simultaneously.

To obtain a reasonable initial value for the set of wavefront coefficient data, the first set of coefficients data calculated from tested wave-front sensing image with a conventional centroid algorithm are used to initialize the optimization step, as already mentioned above.

In reference to FIG. 3, according to a particularly advantageous embodiment of the invention, the calculation of the merit function comprises the calculation of a criteria defined as a difference of at least one shape parameter of the sensed focus light spots and of the modeled focus light spots.

Therefore, beforehand the calculation of the merit function, the optimizing step further comprises a shape parameter data determining step 113 during which a plurality of spot descriptors are generated, each spot descriptor characterizing shape parameter data of a respective (sensed and modeled) focus light spot.

Each spot descriptor may include a $\alpha$ order moment shape descriptor, $\alpha > 1$, a Fourier shape descriptor or a vector field descriptor.

In a preferred embodiment, as illustrated in FIG. 4, second moment descriptors are used as spot descriptors.

Advantageously, second moment descriptor is less sensitive to noise presented in the wavefront sensing images and the effects of various noises on the measurement method are eliminated. Noise is reduced (and signal to noise ratio increases).

Moreover, advantageously, the use of second moment descriptor allow to reduce the problem dimension of the optimization and allow to extract shape/intensity distribution of individual spot, as illustrated in FIG. 4.

More precisely, a second moment represents the shape (variance) of each focus light (sensed and/or modeled) spot intensity $I(x_i, y_j)$ in three elements (3-tuple) where moments $\mu 20$, $\mu 02$ give the variances about the centroid and the covariance measure is given by $\mu 11$.

A central second moment may be defined by the following relation (6):

Central second moment $$m_{pq} = \frac{\sum_{i=1}^{n}\sum_{j=1}^{m}(x_i - \bar{x})^p(y_j - \bar{y})^q I(x_i, y_j)}{\sum_{i=1}^{n}\sum_{j=1}^{m} I(x_i, y_j)} \bar{x} = \frac{\sum_{i=1}^{m}\sum_{j=1}^{n} x_i I(x_i, y_j)}{\sum_{i=1}^{m}\sum_{j=1}^{n} I(x_i, y_j)}; \quad (6)$$

$$\bar{y} = \frac{\sum_{i=1}^{m}\sum_{j=1}^{n} y_j I(x_i, y_j)}{\sum_{i=1}^{m}\sum_{j=1}^{n} I(x_i, y_j)}$$

where $p + q = 2$; $\bar{x}, \bar{y}$ are the centroids

Due to the normalization by total intensity within one lenslet area, the second moment keep constant if the intensity variation between different focus light spots is caused by uncertain absorption which is assumed unchanged in the region within one lenslet. As a result, we do not need to match intensity distribution of wavefront sensing data image.

Alternatively, since total intensity of the spot is known, it could be included as an extra element in the descriptor tuple. If a covariance matrix C is constructed with the tuple, such as given by the relation (7) below, eigen values l1,l2 and eigen vectors V1(v1,v2),V2(v3,v4) of the covariance matrix represented the lengths and direction of the major and minor axis of an equivalent ellipse, which has same total intensity as the related focus light spot, but with uniform intensity distribution.

$$C = \mathrm{cov}(I(x, y)) = \begin{bmatrix} m_{20} & m_{11} \\ m_{11} & m_{02} \end{bmatrix} \quad (7)$$

$$[V, l] = eigen[C]$$

The equivalent ellipse has the same second moments and centroids as the related focus light spot. FIG. 4 illustrates the equivalent ellipse E. More precisely, major E1 and minor E2 axis of equivalent of ellipse E of a focus light sensed spot are plotted as arrows and overlaid on the focus light sensed spot, the length of the arrow corresponding to the length of the axis.

In an embodiment, using eigen values and vectors, the second moment descriptor is defined by a 4-element tuple (s1,s2,s3,s4) where $S1=l1*v1$; $s2=l1*v2$; $s3=l2*v3$; $s4=l2*v4$ could be employed to describe one focus light spot.

Consequently, the wavefront sensing modeled and sensed image could be reduced to L 4-element tuples, where L is the number of focus light spots.

Furthermore, during the shape parameter data determining step 113, the following steps are implemented.

First, a set of the focus light spots and the corresponding modeled focus light spots are selected.

In a next step, a set of pixels of the optical sensor 21b corresponding to each selected focus light spots and each selected modeled focus light spots are identified.

The next step provides a measure of pixel intensity values for each focus light spot.

Then, second moment data of the pixel intensity values for each focus light spot are generated as spot descriptor of the respective spot.

In the next step, a shape parameter for each selected focus light spots and each selected modeled focus light spots is calculated based upon the second moment data.

According to this embodiment, the merit function is therefore defined with the following expression (9):

$$F = \sqrt{\Sigma_{k=1}^{L} \Sigma_{i=1}^{4} (sm_{ik} - ss_{ik})^2} \quad (9)$$

where:
L is the number of focus light spots in the wave-front sensing image;
sm is a second moment of pixel intensity values for a sensed focus light spot;
ss is a second moment of pixel intensity values for a modeled focus light spot.

As illustrated in FIG. 3, when the predetermined condition on the merit function is satisfied (arrow Yes), an optimized set of wave-front coefficient data and an optimized optical parameter value are determined.

More particularly, in an embodiment, the method further comprises a reflective layer of eye model selection step during which a particular reflection layer of the multilayer eye model is chosen.

The next step 114 comprises the selection of the optimized set of wave-front coefficient data and the optimized optical parameter value being characteristic of said selected reflective layer.

The step of obtaining wave-front aberration data 106 comprises the determination of wave-front aberration data of the tested human eye being characteristic of said selected reflective layer.

AS will be apparent to one skilled in the art, the method of the invention may be used in many applications such as vision diagnosis and/or vision corrections systems.

More particularly, the method further comprises a step during which aberration's corrections for the tested human eye from the determined wave-front aberration data are determined.

As illustrated in FIG. 2, the aberration's corrections may be sent to an external unit 28.

In a first example of application, said external unit 28 may be a control unit that controls a compensating optical device and the aberration's corrections are sent in order to provide compensation for said determined wave-front aberration data of the tested human eye.

In a second example of application, said external unit 28 may be a control unit of a lenses manufacturing system and the aberration's corrections are sent in order to manufacture lenses that correct the wave-front aberration data of the tested human eye.

In a third example of application, said external unit 28 may be a control unit associated with a surgery instrument and the aberration's corrections are sent in order to perform surgery on the tested human eye to correct, in real time or not, the wave-front aberration data of the tested human eye.

The one of skill in the art will appreciate the method according to the invention which improves the accuracy of the wavefront aberrations measurements by weakening the influence of noise in said measurements. The quality and the accuracy of wavefront reconstruction are improved.

Furthermore, it will be appreciated by one of skill in the art that the method of the invention could restore optical parameters of eye model such as the axial separation between two reflective layers accurately and precisely without being hindered by the presence of high order aberration.

FIGS. 5 to 7 illustrate some non limitative examples of results that show the efficiency, the robustness and the repeatability of the method according to the invention.

As shown in FIG. 5, known and optimized Zernike coefficients $C_2^0$ of anterior and posterior reflectors of a multilayer eye according to the invention, as well as $C_2^0$ determined by a conventional centroid algorithm, are listed.

Observed wavefront sensing image was simulated with two sets of pre-determined Zernike coefficients by a Shack-Hartman simulator. Wavefront sensing modeled image was simulated by the same simulator but with two sets of Zernike coefficients which are set as random variable.

The derived results are close to the known defocus with the maximum error about 0.06%, and the fitting error (SSE) is only 0.0074. However, the defocus recovered by centroid method is only half of the known amount, and misinterprets the observed image. These results illustrate the drawbacks of conventional analysis that are overcome by the method according to the invention.

In addition, FIGS. 6 and 7 illustrate a reconstructed wavefront from an eye model using a conventional centroid algorithm and the method according to the invention respectively.

With both low and high order aberration presence, conventional centroid algorithm could retrieve most of the aberration except defocus, which was misinterpreted as midpoint of the bi-layer reflector as circled in FIG. 6.

On the contrary, the global algorithm could not only recover the high order aberration with better accuracy but also the defocus, which coincided with the Zernike coefficients producing the data image.

The invention has been described above with the aid of embodiments without limitation of the general inventive concept.

Many further modifications and variations will suggest themselves to those skilled in the art upon making reference to the foregoing illustrative embodiments, which are given by way of example only and which are not intended to limit the scope of the invention, that being determined solely by the appended claims.

In the claims, the word "comprising" does not exclude other elements or steps, and the indefinite article "a" or "an" does not exclude a plurality. The mere fact that different features are recited in mutually different dependent claims does not indicate that a combination of these features cannot be advantageously used. Any reference signs in the claims should not be construed as limiting the scope of the invention.

The invention claimed is:

1. A method for determining wave-front aberration data of a to-be-tested optical system comprising the steps of:
   a) providing a wave-front sensing image of light received from the tested optical system;
   b) providing a model representative of the optical system with at least an optical parameter representative of said model; and
   c) optimizing a set of wave-front coefficient data and said at least optical parameter of said model according to a merit function, wherein the calculation of said merit function comprises the steps of:
   generating a wave-front sensing modeled image of light received from said model by means of said at least optical parameter and said set of wave-front coefficient data; and
   calculating a criteria based on shape parameter data of the wave-front sensing image and shape parameter data of the wave-front sensing modeled image, so as to obtain wave-front aberration data of the tested optical system,
   wherein said wave-front sensing image comprises an array of sensed focus light spots;
   wherein said wave-front sensing modeled image comprises an array of modeled focus light spots; and
   wherein the calculation of the criteria comprises the step of calculating a difference at least between a shape parameter of the sensed focus light spots and of the modeled focus light spots.

2. The method of claim 1, wherein said model is an eye model comprising n reflective layers, n>1.

3. The method of claim 2, wherein at least two of the reflective layers reflect light with different directionalities.

4. The method of claim 2, wherein generating the wave front sensing modeled image comprises:
   obtaining a wave-front sensing image of light received from each illuminated reflective layer of said eye model; and
   generating a wave-front sensing composite modeled image from the wave-front sensing images of the n reflective layers.

5. The method of claim 2, wherein the optical parameter characterizing said eye model is representative of the relative position between two reflective layers.

6. The method of claim 2, wherein the step of obtaining wave-front aberration data comprises:
   selecting a reflective layer of said eye model and obtaining wave-front aberration data from the set of wave-front coefficient data being characteristic of said selected reflective layer.

7. The method of claim 1, wherein the step c) comprises:
   a shape parameter data determining step during which a plurality of spot descriptors are generated, each spot descriptor characterizing shape parameter data of a respective focus light spot and, each spot descriptor including an $\alpha$ order moment shape descriptor, $\alpha>1$, a Fourier shape descriptor or a vector field descriptor.

8. The method of claim 7, wherein the shape parameter data determining step comprises:
   measuring pixel intensity values for each focus light spot, and
   generating second moment data of the pixel intensity values for each focus light spot as a spot descriptor of the respective spot, the second moment data being a second order moment shape descriptor of the respective spot.

9. The method of claim 8, wherein the merit function is defined with the following expression (9):

$$F = \sqrt{\sum_{k=1}^{L} \sum_{i=1}^{4}(sm_{ik} - ss_{ik})^2} \qquad (9)$$

where:
   L is the number of focus light spots in the wave-front sensing image;
   sm is a second moment of pixel intensity values for a sensed focus light spot;
   ss is a second moment of pixel intensity values for a modeled focus light spot.

10. The method of claim 1 wherein the method further comprises:
   a repositioning step of a pupil of said model so as to match the position of the pupil of the tested optical system as it is observed in the provided wave-front sensing image.

11. The method of claim 1, wherein the repositioning step comprises:
   a repositioning step of the array of modeled focus light spots of said model so as to match the position of the array of sensed focus light spots of the tested optical system as it is observed in the provided wave-front sensing image.

12. A non-transitory computer program product comprising one or more stored sequences of instructions that are stored on a non-transitory computer memory and that is accessible to a processor and which, when executed by the processor, causes the processor to carry out at least one of the steps of claim 1.

13. A non-transitory computer readable medium carrying one or more sequences of instructions of the non-transitory computer program product of claim 12.

14. A method to measure the aberrations of an human eye comprising:
   illuminating the human eye under test with light produced by a light source,
   performing the method for determining wave-front aberration data of the tested human eye of claim 1, and
   determining the aberration's corrections for the tested human eye from the determined wave-front aberration data.

15. A method to correct the aberrations of a human eye comprising:
- illuminating the human eye under test with light produced by a light source,
- performing the method for determining wave-front aberration data of the tested human eye of claim 1,
- determining the aberration's corrections for the tested human eye from the determined wave-front aberration data,
- receiving said aberration's corrections:
    - to control a compensating optical device to provide compensation for said determined wave-front aberration data of the tested human eye or;
    - to manufacture lenses that correct said aberrations or;
    - to perform surgery on the tested human eye to correct said aberrations.

* * * * *